United States Patent [19]

Van Der Brug et al.

[11] Patent Number: 5,060,246
[45] Date of Patent: Oct. 22, 1991

[54] COMPUTER TOMOGRAPHY SYSTEM WITH A SCANOGRAM

[75] Inventors: Willem P. Van Der Brug; Jan Timmer; Petrus N. J. Vis, all of Eindhoven, Netherlands

[73] Assignee: U.S. Philips Corporation, New York, N.Y.

[21] Appl. No.: 354,005

[22] Filed: May 19, 1989

[30] Foreign Application Priority Data

Oct. 18, 1988 [NL] Netherlands ............ 8802556

[51] Int. Cl.⁵ ............ G21K 5/02; G21K 5/10
[52] U.S. Cl. ............ 378/20; 378/10; 378/24; 378/21; 378/25
[58] Field of Search ............ 378/11, 10, 15, 25, 378/24, 20, 21, 124, 125, 126, 143, 5, 7, 14, 92, 98, 4, 90, 162, 9, 62, 19, 22

[56] References Cited

U.S. PATENT DOCUMENTS

| | | | |
|---|---|---|---|
| 2,671,867 | 3/1954 | Atlee | 378/143 |
| 3,746,872 | 7/1973 | Ashe et al. | 378/21 |
| 4,045,672 | 8/1977 | Watanabe | 250/360 |
| 4,114,041 | 9/1978 | Oliver | 378/07 |
| 4,477,922 | 10/1984 | Liebetruth | 378/4 |
| 4,485,480 | 11/1984 | Kohno et al. | 378/22 |
| 4,570,264 | 2/1986 | Liebetruth | 378/20 |
| 4,766,603 | 8/1988 | Okabe et al. | 378/162 |
| 4,926,452 | 5/1990 | Baker et al. | 378/22 |

FOREIGN PATENT DOCUMENTS 1098796  8/1955  France .................. 378/24

Primary Examiner—Edward P. Westin
Assistant Examiner—Don Wong
Attorney, Agent, or Firm—William Squire

[57] ABSTRACT

A computer tomography system includes an X-ray tube having an elongate anode across which a beam spot can be displaced, a scanogram being formed by correctly shifting the profiles measured in the various source positions with respect to one another, followed by superposition. Parts of the object which are situated in a selected layer are thus emphasized in an image, parts of the object which are situated outside the selected layer being blurred. When a point of interest in the object is determined by observation of the scanogram, the same apparatus is used to produce a tomography slice image transverse the scanogram image. An important additional advantage consists in that the permissible power to be applied to the X-ray source may be higher. Furthermore, a scanogram thus obtained is not necessarily disturbed by the failure of one or more detectors.

6 Claims, 1 Drawing Sheet

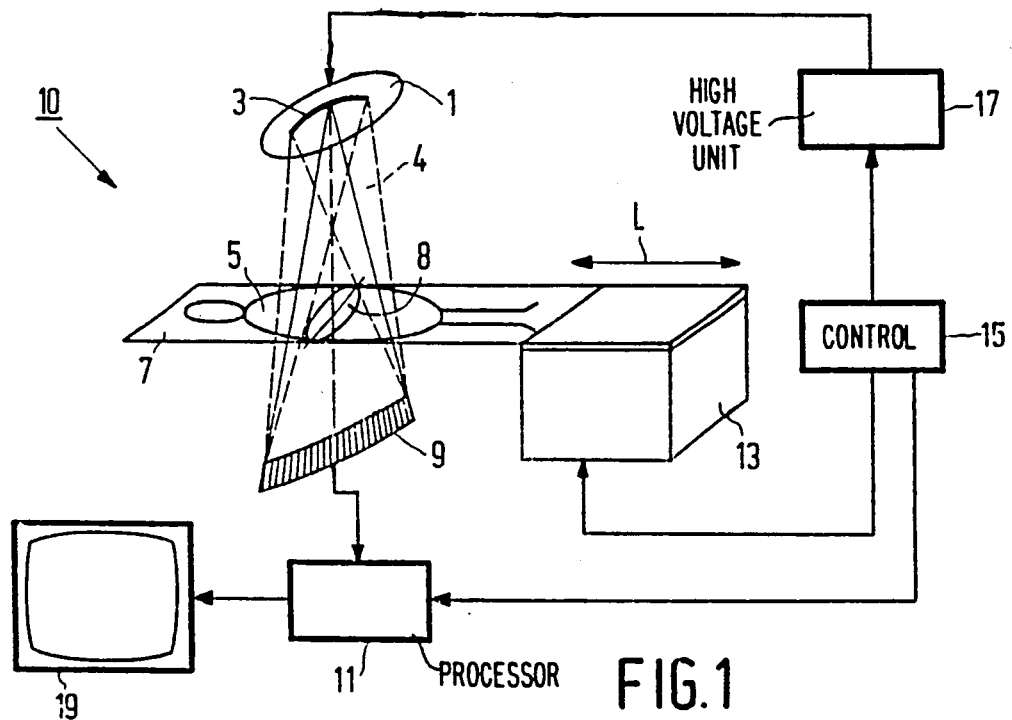
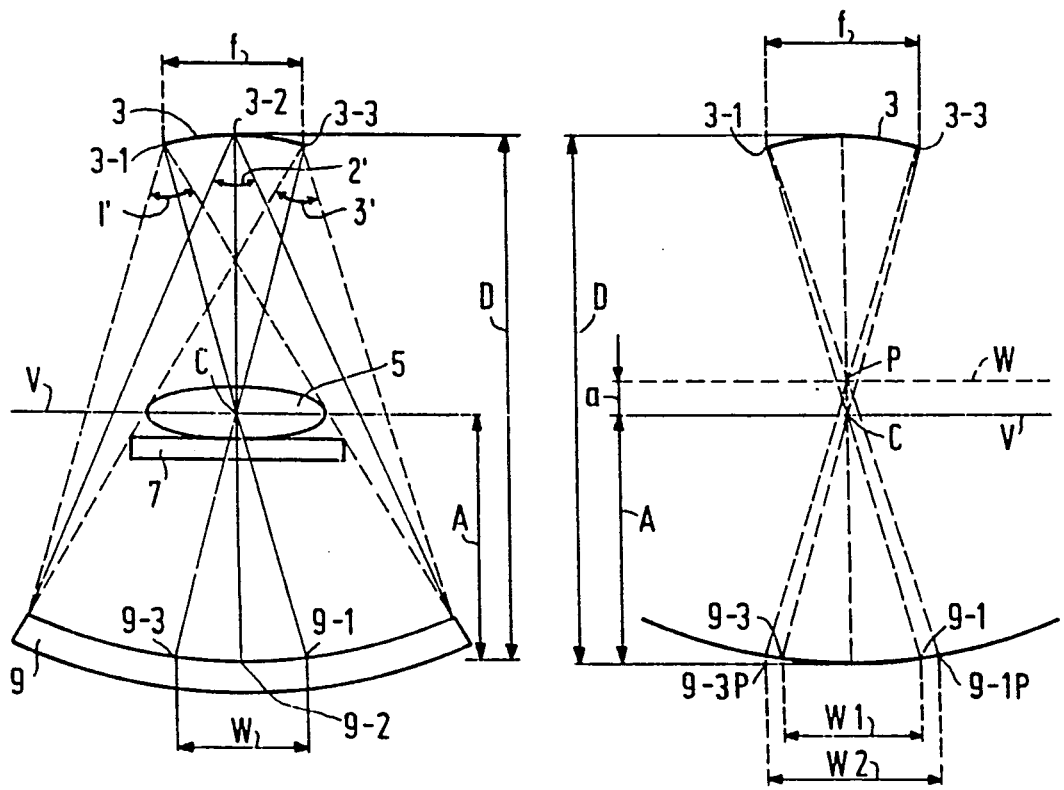

COMPUTER TOMOGRAPHY SYSTEM WITH A SCANOGRAM

The invention relates to a computer tomography device for determining a radiation absorption distribution in a transverse slice of an object, which device comprises an X-ray source and detector means for irradiating the object from a plurality of different directions and for detecting the radiation having passed the object, and also comprises an object carrier and displacement means for displacing the object and the object carrier in a direction transversely of the irradiation direction of the X-ray source.

A computer tomography device of this kind is known from German Patent Application 26 13 809 which corresponds to U.S. Pat. No. 4,477,922. Via the object carrier, the object is displaced transversely of the irradiation direction of the radiation source by the displacement means, the radiation source and the detector means occupying a stationary position, in order to obtain a two-dimensional shadow image of the object. Using this two-dimensional shadow image, the object position of interest can be determined in which an object slice is situated for which an absorption distribution in a given plane is to be determined. Such a two-dimensional shadow image is referred to as a scanogram hereinafter. Like any other shadow image formed by means of a conventional X-ray apparatus, a scanogram has the drawback that the various parts of an object, situated above one another when looking in the direction from the detector to the X-ray source, are imaged in a superposed fashion in a shadow image. As a result, one part of the object may completely mask another part of the object. Due to such masking, the scanogram fails to offer sufficient information for making a useful slice image of the object transverse the scanogram image in the desired location for the purpose of providing an absorption distribution.

The invention has for its object to provide a computer tomography device enabling the formation of a scanogram in which the information can be emphasized in a given layer which extends transversely of the irradiation direction of the X-ray source.

To achieve this, the computer tomography device in accordance with the invention is characterized in that the X-ray source and detector means are arranged each at a respective side of the object, the X-ray source irradiating the object from different directions after a translation of the object, the device also comprising arithmetic means for combining the detector signals, generated in the different directions, so as to obtain a semi-scanogram in which an object layer is emphasized which is to be selected in advance and which extends substantially transversely of the plane of the irradiation directions.

It is to be noted that a tomography device comprising an X-ray tube having an elongate anode which is scanned by an electron beam is known from German Patent Application 25 51 322; however, the scanning motion of the electron beam on the anode thereof always takes place simultaneously with the rotary motion of the X-ray source and the detector means around the object in order to achieve a desired measuring path distribution within the object for the reconstruction of a transverse slice image thereof.

The invention will be described in detail hereinafter with reference to the drawing; therein FIG. 1 diagrammatically shows a device in accordance with the invention, FIG. 2 is a geometrical illustration of the calculation of a tomosynthetic scanogram, and FIG. 3 diagrammatically shows the geometry of the invention for determining the blurring factor in a tomosynthetic scanogram.

FIG. 1 shows a computer tomography device in accordance with the invention, comprising an X-ray source 1 having an elongate anode 3 for generating a diverging, flat X-ray beam 4 which, after having passed an object 5 arranged on an object carrier 7, is detected by an array of detectors 9 arranged in an arc about central point c (FIG. 2). Through the detection of X-rays the detectors 9 generate signals which are stored by a processing device 11. The object carrier 7 is displaced by translation means 13 preferably in monotonous motion in a direction which is denoted by the reference L and which extends transversely of the radiation plane of the X-ray source 1. The computer tomography device 10 also comprises a control unit 15 which generates control signals for the high-voltage unit 17, the translation means 13 and the processing unit 11 in order to synchronize the generating of the X-ray beam, the translation of the carrier 7 and the processing of the measuring signals generated by the detectors 9. From the detector signals the processing unit 11 calculates a scanogram which is displayed on a display device 19. The scanogram is an image lying in a plane V parallel to directions L. The tomography device 10 also comprises known rotation means for rotating the X-ray source 1 and the detector means 9 around the object 5 in order to make a sectional tomography image of the radiation absorption distribution in a plane 8 defined by the flat, diverging beams 4. This image is transverse the scanogram image. It should be understood that the tomograph image requires details in layers outside the scanogram plane whereas the scanogram is most useful when layers outside the scanogram plane are blurred. Normally, two different apparatuses are used to produce a scanogram image and a section tomography image transverse the scanogram. Such rotation means and the processing of the signals thus generated for producing the sectional image are known and will not be elaborated or shown in this Figure.

However, it is known, for example, that such rotation is typically a greater angular extent than that required for a scanogram. Preferably this motion is monotonous.

FIG. 2 diagrammatically shows the elongate anode 3, the array of detectors 9, the object 5 and the object carrier 7, viewed in the longitudinal direction of motion L (see FIG. 1) for generating a scanogram with an apparatus normally used for providing an absorption distribution in a plane transverse directions L. Furthermore, FIG. 2 shows three diverging X-ray beams 1; 2; and 3; which are successively generated, each time at a different point of a path f defined by the elongate stationary anode 3. The beam is produced by an electron spot moving along the anode. These three points 3-1, 3-2, 3-3 are situated at one end, at the center and at the other end of the path f defined by the elongate anode 3. When a plane V is selected in the object 5 at a distance A from the detector array 9, a central point c of the relevant plane is imaged on the detector elements 9-1, 9-2 and 9-3 by the central X-rays from the points 3-1, 3-2 and 3-3, respectively. The distance between the elongate anode 3 and the detector array 9 amounts to D. When the length of the path followed by the electron beam emitted by the anode 3 is f, the distance W between the extreme detector elements 9-1 and 9-3 equals $A \times f/(D-A)$.

From the three shadow profiles obtained in the source positions 3-1, 3-2 and 3-3 by detection of the radiation beams 1, 2, and 3' by the array i.e., a scanogram portion at this position of detectors 9, a semi-scanogram of the layer at plane V can be constructed in which the parts which are situated in the layer at plane V of the object 5 are clearly shown and the parts of the object which are situated above and below the layer at plane V are blurred. This emphasized imaging of the layer at plane V is achieved by shifting and superposing the three different profiles obtained by means of the measuring beams 1, 2, and 3 with respect to one another. When the profile I is shifted to the right over a distance equal to half the distance W and the profile 3 is shifted to the left over a distance equal to half the distance W, the images of the point c of the three profiles will conincide. It can be demonstrated that this also holds good for other points situated in the plane V. It will be apparent that it is also possible to abstain, for example from shifting the profile measured by means of the beam 1 and to shift the profiles measured by means of the beams II and III over one half W and W, respectively. Generally speaking, when the number of profiles measured in different source positions amounts to N, a profile must be shifted over a distance equal to $i \times W/N$ in order to achieve registration with other profiles, resulting in a semi-scanogram with a better image of the plane V. Therein, i is the profile number measured in the $i^{th}$ source position, one extreme source position (in this case 3-1 or 3-3) being assigned the index number 0.

FIG. 3 geometrically shows the X-ray source and the array of detectors used to blurr a point in a semi-scannogram which is situated below or above the selected plane. FIG. 3 shows two source positions on the elongate anode 3. The positions, having a spacing f, are the positions 3-1 and 3-3 also used in FIG. 2. Two images of a central point c in the plane V are detected by means of the detectors 9-1 and 9-3, again as shown in FIG. 2. The distance between these two images amounts to W1. For a point P which is situated in a plane W above the plane V there are also formed two images, associated with the source positions 3-1 and 3-2, these images being obtained in the detector positions 9-1P and 9-3P, respectively. The distance between these two images 9-1P and 9-3P amounts to W2. The distance between the anode 3 and the array of detectors 9 amounts to D, the distance between the plane V and the array of detectors is A, and the distance between the plane V to be imaged and the plane W to be blurred is a. The distance W1 between the imaging positions 9-1 and 9-3 amounts to $A \times f/(D-A)$. The distance W2 between the two imaging points 9-1P and 9-3P amounts to $(A+a) \times f/(D-(A+a))$. A blurring factor can now be calculated which indicates the degree of blurring of the plane W. When the blurring factor DF is defined as the difference between W2 and W1, it can be calculated that DF equals $f \times a \times D/(D-A-a)(D-A)$. It can be deduced therefrom that the blurring DF is more pronounced as the distance f between the extreme source positions 3-1 and 3-3 increases, the distance a between the plane W to the blurred and the desired plane V increases, and the ratio of the distance A between the plane V and the array of detectors 9 and the distance D between the elongate anode 3 and the detector array 9 increases.

The computer tomography device in accordance with the invention offers the advantage that a scanogram can be made of a plane V where parts of the object situated in this plane are imaged in focus, object parts outside the plane V being imaged in a more or less blurred fashion. The device in accordance with the invention offers other advantages, because during the formation of the scanogram the anode 3 of the X-ray tube is no longer continuously irradiated in one position, but sequentially in different positions. Because of this movement of the focal spot across the X-ray anode, the energy applied to the anode is distributed among a number of locations, thus reducing the local load of the anode. Local burning of the anode by excessive bombardment with the electron beam is thus avoided. The directions in which the object is irradiated is preferably the same after each translation. A further advantage is the following. When a scanogram is made according to the state of the art, the failure of one or more detectors will become manifest as straight lines in the scanogram, which lines are reproduced either as completely dark lines or as completely light lines. In the case of failure of a detector in the computer tomography device in accordance with the invention, however, a new calibration can be applied in order to prevent incorrect signals supplied by the faulty detector from spoiling the tomosynthetic scanogram. One of the possibilities of realizing a non-disturbed scanogram in the event of incorrect detector signals is to ignore these signals completely and to standardize the intensity of the signals in the pixels of the scanogram to the number of detectors having contributed to the signal strength in the relevant pixel.

In a computer tomography device comprising an X-ray source having an elongate anode which is irradiated during rotation of the X-ray source around the object in order to realize a scanogram, the scanning direction of the electron beam across the elongate anode preferably opposes the direction of rotation of the X-ray tube, because the spacing f is then maximum, so that the blurring of the object elements situated outside the plane V is also maximum.

We claim:

1. A computer tomography system comprising:
   first means for producing a radiation attenuation distribution image in a transverse slice of an object, said means comprising an X-ray source for irradiating an object in a plurality of directions in a plane about an axis and detector means for detecting the radiation passed through the object and for producing signals representing said detected radiation in said plurality of directions;
   an object carrier between said source and detector;
   displacement means for displacing the object carrier in a direction transverse said plane; and
   second means responsive to said source and detector means for creating in response to said detector signals a second image of said object extending substantially normal to said plane, said second means including means for emphasizing a given object layer by causing overlying adjacent layers of said second image to be blurred and arithmetic means for combining in superposition the detector signals generated in said plurality of directions to form said second image as a composite semi-scanogram image of said object.

2. A computer tomography system as claimed in claim 1, wherein the directions in which the object is irradiated are the same after each displacement.

3. A computer tomography system as claimed in claim 1 or 2, wherein the displacement is a continuous motion.

4. A computer tomography system as claimed in claim 1 or 2, wherein the X-ray source and the detector means perform continuous rotation.

5. A computer tomography system as claimed in claim 1 or 2, wherein that the X-ray source is an X-ray tube comprising an elongate anode which extends transversely of the displacement direction and which is struck by an electron beam in different locations.

6. A computer tomography system as claimed in claim 5, wherein the anode is scanned during a rotation of the X-ray source around the object, the scanning direction of the electron beam on the elongate electrode opposing the direction of rotation of the X-ray tube.

* * * * *